United States Patent [19]

Kobzina

[11] 4,309,209

[45] Jan. 5, 1982

[54] HERBICIDAL METHOD AND COMPOSITION

[75] Inventor: John W. Kobzina, Walnut Creek, Calif.

[73] Assignee: Chevron Research, San Francisco, Calif.

[21] Appl. No.: 824,598

[22] Filed: Aug. 15, 1977

[51] Int. Cl.³ ............................................. A01N 43/82
[52] U.S. Cl. ........................................................ 71/91
[58] Field of Search ....................................... 71/91, 90

[56] References Cited

U.S. PATENT DOCUMENTS

| | | | |
|---|---|---|---|
| 3,495,967 | 2/1970 | Driscoll et al. | 71/91 X |
| 3,557,133 | 1/1971 | Holtschmidt et al. | 71/90 X |
| 3,574,226 | 4/1971 | Ratz et al. | 260/302 D |

FOREIGN PATENT DOCUMENTS 2109755 9/1972 Fed. Rep. of Germany .

OTHER PUBLICATIONS

Ried et al., Angew. Chem. International Edition (1976), pp. 103-104.

*Primary Examiner*—Catherine L. Mills
*Attorney, Agent, or Firm*—J. A. Buchanan, Jr.; D. A. Newell; T. G. DeJonghe

[57] ABSTRACT

The growth of undesired vegetation is inhibited by applying to the locus where such growth is not desired an herbicidally effective amount of a compound of the formula

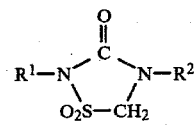

wherein $R^1$ is methyl or ethyl and $R^2$ is phenyl; or phenyl substituted with 1 to 2 halogen atoms, 1 to 2 alkyl groups of 1 to 2 carbon atoms, or 1 to 2 alkoxy groups of 1 to 2 carbon atoms.

12 Claims, No Drawings

HERBICIDAL METHOD AND COMPOSITION

BACKGROUND OF THE INVENTION

The present invention relates to the use of certain thiadiazolidines as herbicides, especially as pre-emergent herbicides and to herbicidal compositions containing certain thiadiazolidines. The invention also relates to a process for preparing the thiadiazolidines.

Prior art references concerning herbicidal compositions are numerous. For example, U.S. Pat. Nos.: 3,766,202; 3,796,561; 3,822,282; 3,854,925; and 3,925,553 relate to the use of herbicides containing various substituted amino-imidazolidinediones. Prior art relevant to the structure of the compounds contained in the herbicidal composition of the present invention and used in the process of the present invention includes Angew. Chem. International Edition, 1976, "Novel 1,2,4-Thiadiazolidine 1-Oxides and 1,1-Dioxides from 2-Imino-1,3-thiazetidines," by Walter Ried et al, pages 103–104. This latter reference discloses a compound having the same general formula as the compounds used in the present invention and wherein $R^1$ is methyl and $R^2$ is phenyl which is, thus, identical to one of the preferred compounds contained in the herbicidal composition of the present invention.

SUMMARY OF THE INVENTION

According to the present invention a method of inhibiting the growth of undesired vegetation is provided which comprises applying to the locus where such growth is not desired a herbicidally effective amount of a compound of the formula

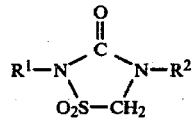

wherein $R^1$ is methyl or ethyl and $R^2$ is phenyl; or phenyl substituted with 1 to 2 halogen atoms, 1 to 2 alkyl groups of 1 to 2 carbon atoms, or 1 to 2 alkoxy groups of 1 to 2 carbon atoms. Preferably, the $R^2$ group is phenyl or phenyl substituted with 1 to 2 of fluoro, chloro or bromo. Particularly preferred compounds for use in the present invention are those wherein $R^1$ is methyl and $R^2$ is phenyl or phenyl substituted with fluoro or chloro.

I have discovered that there is much better herbicidal activity for the present type compounds when $R^1$ is methyl than when it is propyl, specifically propyl attached via the secondary carbon atom. Thus, as will be seen from the Table hereinbelow, the herbicidal effectiveness of compounds wherein $R^1$ is methyl, for example compound B, was about 300% greater than that for compound G which had a propyl group in the $R^1$ position. For both compounds B and G the $R^2$ group was phenyl. Comparisons of results using compounds A vs. F; and C vs. H, also bears out this same conclusion.

According to a preferred embodiment of the present invention, a herbicidal composition is provided, which composition comprises an inert carrier and, in a herbicidally effective amount, a compound of the formula

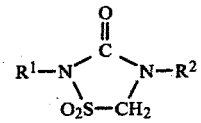

wherein $R^1$ is methyl or ethyl and $R^2$ is phenyl; or phenyl substituted with 1 to 2 halogen atoms, 1 to 2 alkyl groups of 1 to 2 carbon atoms, or 1 to 2 alkoxy groups of 1 to 2 carbon atoms. Preferred $R^1$ and $R^2$ groups for the herbicidal composition are as mentioned above with respect to the method of inhibiting undesired vegetation growth.

A particularly preferred embodiment for the herbicidal composition is as a wettable powder. The wettable powder desirably contains the above-mentioned herbicidally-active compound and an inert carrier such as kaolin clay, talc, atapulgite, calcium carbonate or magnesium carbonate. Kaolin clay is an especially preferred inert carrier. Also, desirably the composition contains a surfactant or dispersing agent such as are known in the art for aiding the dispersion of the finely-divided powder ingredients of the composition in a solvent such as water. The surfactant may be of the nonionic type or the ionic type and can be selected from materials such as calcium alkyl sulfonates or sodium lauryl sulfonate, or a lignosulfonate salt.

Preferred amounts of the ingredients of the composition are 1–90% active compound, 10–95% inert carrier and 0.5–15% surfactant. More preferred ranges are 10–80% active, 20–90% inert carrier and 1–9% surfactant. Particularly preferred wettable powder herbicidal compositions of the present invention contain about 40–60% active, 40–60% inert carrier and 2–8% surfactant. Percentages in this specification are by weight unless indicated otherwise.

The herbicidal composition of the present invention may alternatively be formulated as a "flowable" with either an oil or water base. In the instance of a flowable herbicidal composition, the oil or water base is considered, for purposes of the present specification, as the inert carrier. Desirably, the flowable composition will also contain a suspending agent or thickener. Types of suspending agents known in the art include the following: density suspension, clay suspension, polymer suspension or surfactant suspension.

Preferably, the flowable herbicidal composition in accordance with the present invention contains 20–70% active, 30–80% inert carrier (oil or water base), and 1–10% suspending agent.

In the case of either the wettable powder or the flowable herbicidal composition of the present invention, preferably the active compound is micronized; that is, very finely divided into particle sizes between about 0.5 and 20 microns, more preferably between 2 and 8 microns, for purposes of formulating the final herbicidal composition.

According to another embodiment of the present invention, a process is provided for preparing compounds of the formula

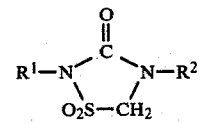

which process comprises contacting and reacting a phenyl or substituted phenyl isocyanate with an N-alkylchloromethanesulfonamide wherein $R^1$ is $C_1$-$C_6$ alkyl; $C_3$-$C_6$ cycloalkyl; benzyl; or one of the foregoing groups substituted with 1-5 chlorine, bromine or fluorine atoms, and $R^2$ is $C_1$-$C_6$ alkyl or one of the foregoing substituted with 1-5 chlorine, bromine or fluorine atoms. Preferably $R^1$ is methyl or ethyl and $R^2$ is phenyl; or phenyl substituted with 1 to 2 halogen atoms, 1 to 2 alkyl groups of 1 to 2 carbon atoms, or 1 to 2 alkoxy groups of 1 to 2 carbon atoms. Particularly preferred $R^1$ and $R^2$ groups are as stated for the herbicidal composition.

The preparation reaction may be summarized by the following reaction equation:

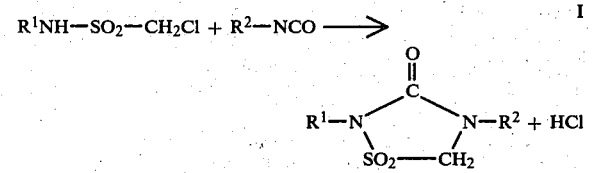

This reaction sequence may be contrasted to the reaction sequence in the previously cited Walter Ried et al Angew. Chem. reference wherein a thiadiazolidine is prepared from a 2-amino-1,3-thiazolidine in a series of steps using hydrogen peroxide and glacial acetic acid. The above reaction sequence may also be contrasted to a Russian reference "Reaction of Azomethines with Acyl Isocyanates in Presence of Sulfur Dioxide" by B. A. Arbuzov et al. In the Russian reference, a thiazolidine compound is obtained in a series of reaction steps involving the reaction of a Schiff base with an acyl isocyanate in the presence of $SO_2$.

Referring again to the Equation I, that is, the reaction used in the reaction process of the present invention, preferably, the reactants are present in equal molar amounts, although a small excess of either one may be employed. Desirably, the reaction is carried out in the presence of a basic substance which acts as an HCl scavenger or neutralizer. Preferably, at least one equivalence and even two or more equivalences of a liquid base are used, and this substance then functions both as a solvent and as an acid neutralizer. Compounds useful for this purpose are the basic organic amines preferably the tertiary amines, such as pyridine, triethylamine, triethylene diamine, N-methyl piperidine, etc. Inert solvents such as diethyl ether, tetrahydrofuran, and the like may also be employed in addition to the amine.

The reaction desirably is carried out at temperatures within the range 0° C. to 50° C., preferably 10° C. to 25° C. This reaction is exothermic, and cooling of the reaction mixture prior to or during reaction provides the necessary control. Preferably the reaction is kept at about room temperature for ½ to 24 hours, preferably 1 to 2 hours.

The pressure on the reaction may be either greater or less than atmospheric, e.g., 1 to 100 psia, but is preferably atmospheric pressure.

Product workup comprises washing the crude reaction mixture with water to remove the amine hydrochloride and any excess amine. The crude product is obtained as a solid material, which after drying is satisfactory for use in the present invention. However, the crude product may be further purified by recrystallization from an appropriate solvent such as ethanol.

The aromatic isocyanate feedstock is a readily available material being obtained from the reaction of phosgene with aniline or an aniline derivative.

The N-alkyl chloromethane sulfonamides are prepared by the reaction of chloromethane sulfonyl chloride with an appropriate primary amine, e.g., methyl- or ethyl-amine, see Equation II. Excess amine, preferably at least 2 equivalences, are used in order to neutralize the by-product HCl by forming an amine hydrochloride.

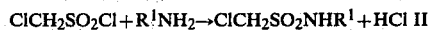

$$ClCH_2SO_2Cl + R^1NH_2 \rightarrow ClCH_2SO_2NHR^1 + HCl \quad II$$

This reaction is preferably carried out in a large volume of a low-boiling liquid solvent such as ether, dichloromethane, chloroform, etc., in which the amine hydrochloride is insoluble. The reaction temperature is kept below 0° C. during the mixing of the reactants, for example by the use of a dry ice bath. After complete mixing, the reaction is allowed to slowly warm to room temperature. Reaction times of 1 to 24 hours at room temperature may be employed; generally about 2 to 4 hours are sufficient for good yields. The crude product is obtained as an oily liquid by first filtering off the precipitated amine hydrochloride and then distilling off the low-boiling solvent. This crude material is of satisfactory purity for use in the subsequent cyclization reaction.

EXAMPLES

Example 1: Preparation of N-methyl-chloromethane-sulfonamide

A 3-liter 3-necked round-bottom flask, equipped with a stirrer, thermometer, condenser, dropping funnel and a gas inlet tube was charged with 2 liters of dichloromethane. After this was cooled in an acetone-dry ice bath, 41.6 grams (1.34 mols) of methylamine was added through the gas inlet. Then 80 grams (0.54 mol) of chloromethane sulfonyl chloride was added dropwise to the well-stirred solution while the temperature was kept below 0° C. After all of the sulfonyl chloride was added, the temperature was brought to 25° C., and stirring was continued at this temperature for 2 hours.

At the end of this time, the reaction mixture was filtered. The dichloromethane was removed by gently heating under a vacuum. The resulting crude N-methyl chloromethane sulfonamide was a clear brown liquid which had an NMR spectra and an infrared spectra consistent with the assigned structure.

Example 2: Preparation of 4-p-chlorophenyl-1,2,4-thiadiazolidine-1,1,3-trione A 50-ml flask was charged with 5.0 grams (0.035 mol) of N-methyl chloromethane sulfonyl chloride (from Example 1) and 5.3 grams (0.035 mol) of p-chlorophenylisocyanate. Then 3 ml of triethylamine were added. There was an exothermic reaction, and the mixture turned solid. After standing for ¾ hour at 25° C., ether was added to form a slurry. This slurry was filtered to give a white solid which was reslurried in ether, filtered and dried to give 2.7 grams of 4-p-chlorophenyl-1,2,4-thiadiazolidine-1,1,3-trione having a melting point of 155°-157° C. Analysis for $C_9H_9ClN_2O_3S$: S, 12.3%; Cl, 13.6%. Found, S, 12.4%; Cl, 13.7%. The infrared spectra had strong absorption at 1720, 1485, 1435, 1370, 1340, 1280, 1255, and 1145 $cm^{-1}$. The NMR spectra in 6D-dimethylsulfoxide had major peaks at 7.7

(4H), 5.6 (2H), and 3.3 (3H) ppm, and minor peaks at 4.0 and 2.8 ppm.

Example 3

Various thiadiazolidines were prepared and tested for biological activity. The compounds prepared and herbicidal results using them are summarized in Tables I and II below.

present invention. Compounds K and L of Table II can be contrasted respectively to compounds B and A of Table I; compounds K and L are similar to compounds B and A except that the carbonyl group or the diazo ring is replaced by a C=S group. Compounds K and L were found to give very low or nil herbicidal activity and these compounds are outside the scope of the compounds used in the present invention.

TABLE I

| RE No. | Compound | $R^1$ | $R^2$ | Herbicidal Activity Pre-Emergent Control/Post-Emergent Control | | | | | |
|---|---|---|---|---|---|---|---|---|---|
| | | | | WO | WG | CG | M | PW | LQ |
| 22,725 | A | Me | p-chlorophenyl | 25/0 | 70/0 | 45/0 | 95/0 | 98/0 | 93/0 |
| 22,726 | B | Me | phenyl | 93/0 | 90/0 | 98/0 | 100/35 | 95/40 | 95/65 |
| 22,769 | C | Me | o-fluorophenyl | 100/0 | 95/0 | 98/0 | 95/45 | 98/40 | 98/90 |
| 22,837 | D | Me | 3,4-dichlorophenyl | 0/0 | 0/0 | 0/0 | 10/0 | 40/0 | 40/30 |
| 22,886 | E | Me | 3,5-dichlorophenyl | 0/0 | 0/0 | 0/0 | 10/0 | 85/0 | 80/0 |
| 22,903 | F | 2P | p-chlorophenyl | 0/0 | 0/0 | 0/0 | 0/0 | 0/0 | 0/0 |
| 22,041 | G | 2P | phenyl | 0/0 | 10/0 | 0/0 | 30/0 | 30/0 | 35/0 |
| 22,942 | H | 2P | o-fluorophenyl | 20/0 | 20/0 | 40/0 | 65/30 | 75/30 | 60/45 |
| 22,943 | I | Me | o-methoxyphenyl | 45/0 | 55/0 | 50/0 | 65/0 | 73/0 | 55/0 |
| 22,944 | J | Me | o-methylphenyl | 75/0 | 60/0 | 80/0 | 75/0 | 90/0 | 88/0 |

WO = Wild Oats
WG = Water Grass
CG = Crab Grass
M = Mustard
PW = Pigweed
LQ = Lambsquarter

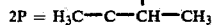

$$2P = H_3C-\underset{\underset{\displaystyle |}{}}{C}-CH-CH_3$$

TABLE II

| RE No. | Compound | $R^1$ | $R^2$ | Herbicidal Activity Pre-/Post-Emergent Control | | | | | |
|---|---|---|---|---|---|---|---|---|---|
| | | | | WO | WG | CG | M | PW | LQ |
| 22,835 | K* | Me | phenyl | 0/0 | 0/0 | 0/0 | 0/0 | 0/0 | 0/0 |
| 22,836 | L* | Me | p-chlorophenyl | 0/0 | 0/0 | 0/0 | 0/0 | 0/0 | 0/0 |
| 22,837 | M | benzyl | o-fluorophenyl | 0/0 | 0/0 | 0/0 | 0/0 | 0/0 | 0/0 |
| 22,888 | N | benzyl | 3,5-dichlorophenyl | 0/0 | 0/0 | 0/0 | 0/0 | 0/0 | 0/0 |
| 22,889 | O | benzyl | p-chlorophenyl | 0/0 | 0/0 | 0/0 | 0/0 | 0/0 | 0/0 |
| 23,205 | P | Me | 4-phenoxyphenyl | 0/0 | 0/0 | 0/0 | 0/0 | 0/0 | 0/0 |

*These compounds, K and L, are thiadiazolidines, i.e., the carbonyl group of the thiadiazolidine ring is replaced by a C=S group.

As can be seen from Table I and as previously mentioned under Summary of the Invention, compounds such as A and B performed very well in terms of herbicidal activity compared to the use of compounds such as F and G. The use of compounds F and G are outside the scope of the embodiments of the present invention relating to a herbicidal method and to a herbicidal composition.

It can also be noted from Table I that the use of compounds such as compound B were found to give very good pre-emergent herbicidal activity compared to only relatively low post-emergent herbicidal activity. Similarly, compound A was even more striking in this regard in that it gave fair to good pre-emergent herbicidal activity but gave no detectable post-emergent herbicidal activity in the test method employed.

Also, it was found that the compounds as used in the present invention gave very low fungicidal activity, very low insecticidal activity, very low miticidal activity and very low nematocidal activity. Thus, in summary, it was found that the high activity of the compounds was in the area of herbicidal activity and this, in turn, was selective for only certain compounds as illustrated by the contrast of compounds A and B to compounds F and G.

Table II presents data for six further compounds related to the compounds used in the method of the present invention. Compounds K and L of Table II can Compounds M, N and O in Table II are also outside the scope of the compounds used in accordance with the present invention. Compounds M, N and O have an $R^1$ group which is benzyl.

The test method for the pre-emergent herbicidal tests and for the post-emergent herbicidal tests were as follows:

Pre-Emergent Test

An acetone solution of the test compound was prepared by mixing 750 mg of the compound, 220 mg of a nonionic surfactant and 25 ml of acetone. This solution was added to approximately 125 ml of water containing 156 mg of surfactant.

Seeds of the test vegetation were planted in a pot of soil and test solution was sprayed uniformly onto the soil surface at a dose of 33 mcg/cm². The pot was watered and placed in a greenhouse. The pot was watered intermittently and was observed for seedling emergence, health and emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Tables I and II.

Post-Emergent Test

The test compound was formulated in the same manner as described above for the pre-emergent test. The concentration of the test compound in this formulation was 5000 ppm. This formulation was uniformly sprayed on 2 similar pots of 24-day-old plants (approximately 15 to 25 plants per pot) at a dose of 33 mcg/cm². After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated on these observations. A 0-to-100 scale was used, 0 representing no phytotoxicity and 100 representing complete kill. The results of these tests appear in Tables I and II.

What is claimed is:

1. A method of inhibiting the growth of undesirable vegetation comprising applying to the locus where such growth is not desired a herbicidally effective amount of a compound of the formula:

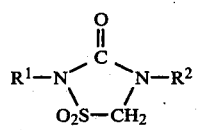

wherein $R^1$ is methyl or ethyl and $R^2$ is phenyl; or phenyl substituted with 1 to 2 halogen atoms, 1 to 2 alkyl groups of 1 to 2 carbon atoms, or 1 to 2 alkoxy groups of 1 to 2 carbon atoms.

2. A method in accordance with claim 1 wherein $R^1$ is methyl.

3. A method in accordance with claim 1 wherein $R^2$ is phenyl or phenyl substituted with 1 to 2 of fluoro, chloro or bromo.

4. A method in accordance with claim 3 wherein $R^2$ is phenyl.

5. A method in accordance with claim 3 wherein $R^2$ is phenyl substituted with 1 fluoro or chloro atom.

6. A herbicidal composition for inhibiting the growth of undesired vegetation comprising an inert carrier and, in a herbicidally effective amount, an active compound of the formula:

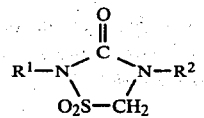

wherein $R^1$ is methyl or ethyl and $R^2$ is phenyl; or phenyl substituted with 1 to 2 halogen atoms, 1 to 2 alkyl groups of 1 to 2 carbon atoms, or 1 to 2 alkoxy groups of 1 to 2 carbon atoms and wherein the composition comprises 1 to 90% by weight of the active compound, 10 to 95% inert carrier and 0.5 to 15% of a surfactant.

7. A composition in accordance with claim 6 wherein $R^1$ is methyl.

8. A composition in accordance with claim 6 wherein $R^2$ is phenyl or phenyl substituted with 1 to 2 of fluoro, chloro or bromo.

9. A composition in accordance with claim 7 wherein $R^2$ is phenyl.

10. A composition in accordance with claim 7 wherein $R^2$ is phenyl substituted with 1 fluoro or chloro.

11. A method of inhibiting the germination or growth of undesirable seeds which comprises applying to the locus where such germination or growth is not desired, prior to the emergence of seedlings from such seeds, a herbicidally effective amount of a compound of the formula

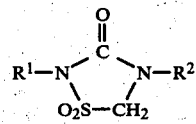

wherein $R^1$ is methyl or ethyl and $R^2$ is phenyl; or phenyl substituted with 1 to 2 halogen atoms, 1 to 2 alkyl groups of 1 to 2 carbon atoms, or 1 to 2 alkoxy groups of 1 to 2 carbon atoms.

12. A method in accordance with claim 11 wherein $R^1$ is methyl and $R^2$ is phenyl.

* * * * *